United States Patent [19]

Gross

[11] Patent Number: 5,158,773
[45] Date of Patent: Oct. 27, 1992

[54] RETINOID ESTERS

[75] Inventor: Günter Gross, Weil am Rhein, Fed. Rep. of Germany

[73] Assignee: Hoffmann-La Roche Inc., Nutley, N.J.

[21] Appl. No.: 663,356

[22] Filed: Mar. 4, 1991

[30] Foreign Application Priority Data

Mar. 27, 1990 [CH] Switzerland ............ 1008/90

[51] Int. Cl.$^5$ .............................. A61K 6/00
[52] U.S. Cl. .................. 424/401; 514/529; 554/221
[58] Field of Search ............ 260/408, 404.5, 410.9 V; 424/401

[56] References Cited

U.S. PATENT DOCUMENTS

| | | | |
|---|---|---|---|
| 4,476,056 | 10/1984 | Pawson | 260/408 |
| 4,888,363 | 12/1989 | Dulak et al. | 424/401 |
| 4,900,478 | 2/1990 | Gross | 260/408 |

OTHER PUBLICATIONS

PCT Application No. WO 88/09788, published Dec. 15, 1988.

*Primary Examiner*—Thurman K. Page
*Assistant Examiner*—William E. Benston, Jr.
*Attorney, Agent, or Firm*—George M. Gould; William H. Epstein; Bruce A. Pokras

[57] ABSTRACT

Retinoids of the formula $R^1\text{—OCH}(R^2)\text{OC(O)}R^3$ wherein $R^1$ signifies 13-cis-retinoyl, $R^2$ signifies hydrogen or lower-alkyl and $R^3$ signifies straight-chain lower-alkyl can be used as medicaments in the case of dermatological disorders.

2 Claims, No Drawings

RETINOID ESTERS

The present invention is concerned with novel retinoids, their manufacture and use for the manufacture of medicaments, as well as medicaments which contain these compounds as active substances.

The retinoids in accordance with the invention can be represented by the general formula:

$$R^1-OCH(R^2)OC(O)R^3 \quad\quad I$$

wherein $R^1$ is 13-cis-retinoyl; $R^2$ is hydrogen or lower-alkyl; and $R^3$ is straight-chain lower-alkyl.

Lower-alkyl groups can contain 1-6 carbon atoms. Methyl, ethyl, propyl, isopropyl, n-butyl, sec-butyl and tert-butyl are examples of lower-alkyl $R^2$ groups. Hydrogen and methyl are the preferred $R^2$ groups. Methyl, ethyl, propyl and n-butyl, preferably methyl, are examples of $R^3$ groups.

The compounds of formula I can be obtained by reacting 13-cis-retinoic acid or a salt thereof with a compound of the formula:

$$XCH(R^2)OC(O)R^3 \quad\quad II$$

or by reacting a compound of the formula:

$$R^1OCH(R^2)X \quad\quad III$$

with a salt of an acid of the formula $R^3COOH$, whereby in the above formulae X is halogen, preferably chlorine or iodine, and $R^1$, $R^2$ and $R^3$ have the significance given above.

Examples of salts of 13-cis-retinoic acid are alkali salts such as the sodium salt or the potassium salt; or trialkylammonium salts, e.g., the triethylammonium salt; or, preferably, salts with 1,8-diazacyclo[5.4.0]undec-7-ene.

The reaction is conveniently carried out in an inert organic solvent, e.g., in acetonitrile, dimethylformamide or acetone. The reaction temperature is not critical. The reaction can be performed at room temperature or while heating, e.g., to the reflux temperature of the solvent which is used.

The compounds of formulae II and III are known or can be prepared in a manner known per se. For example, the compounds II can be prepared by reacting an acid chloride with an aldehyde in the presence of zinc chloride (J. Am. Chem. Soc., 43, 660 (1921),. The chloromethyl ester of 13-cis-retinoic acid can be prepared, e.g., by reacting a salt of 13-cis-retinoic acid with bromochloromethane.

The compounds of formula I are therapeutically active. They can be used, for example, for the treatment of dermatological disorders, especially in the case of acne and those dermatological disorders which are accompanied by cornification disorders of the skin such as, e.g., psoriasis, ichthyosis and Darier's disease and in the case of disorders of fibroblast activities such as, e.g., keloidosis and localized schlerodermia; as well as in the case of precanceroses of the skin.

The compounds of formula I can also be used in the treatment of aging skin.

The novel compounds are especially suitable for topical use. They exhibit a good skin tolerance, good penetration capability and cause no or only a slight systemic retinoid effect.

The efficacy of the compounds can be determined in mice in which papillomas of the skin have been produced by treatment with dimethylbenzantracene and croton oil. By the topical administration of compounds of formula I there is observed a regression of the papillomas, which represents a measurement for the therapeutic efficacy of the compounds, e.g. for the treatment of psoriasis. The test methodology for the production of the papillomas is described in Europ. J. Cancer, Vol. 10,731-737 (1974). The papillomas were treated topically for 3 weeks with different concentrated solutions of the test compounds. Only 3 papillomas of each animal were treated with the test compounds. The remaining papillomas were treated only with the vehicle. Any influence on these papillomas which were not treated topically with the test compounds is due to the systemic effect of the topically-administered test preparation. The results obtained with compounds of formula I in this test model are given in Table I.

TABLE 1

| Compound | Concentration of the applied solution [%] | Change in the papillomas [%]* Treated | Untreated |
|---|---|---|---|
| Vehicle (acetone) | — | +25 | 0 |
| I, $R^2$ = H $R^3$ = $CH_3$ | 0.124 | 0 | 0 |
| | 1.24 | −33 | 0 |
| | 3.1 | −50 | 0 |
| I, $R^2$ = $CH_3$ $R^3$ = $CH_3$ | 0.129 | 0 | 0 |
| | 1.24 | −20 | 0 |
| | 3.2 | −43 | 0 |

*Median value: average value, in respect of which the same number of higher and lower test values exist.

A model for testing the efficacy in the treatment of acne is the change in size of the sebaceous glands in the ear of Syrian golden hamsters after topical application of the test substance. In this test, one ear is treated with active substance solution and the other ear is treated with vehicle. The change in the size of the sebaceous glands is measured on tissue sections by digital planimetry. Any influence on the sebaceous glands of the ear treated only with vehicle is due to a systemic effect. The results obtained with the compound I wherein $R^2$ and $R^3$ are both methyl are compiled in Table II.

TABLE II

| Compound | Dosage [μg/day] | Reduction in sebaceous gland diameter [%] Active substance | Vehicle |
|---|---|---|---|
| I, $R^2$ = $CH_3$ $R^3$ = $CH_3$ | 10 | −41 | −9* |
| | 100 | −45 | −16* |

*Statistically not significant

For topical use the active substances are conveniently used in the form of salves, tinctures, creams, solutions, lotions, sprays, suspensions and the like. Salves and creams as well as solutions are preferred. These preparations specified for topical use can be manufactured by mixing the process products as active ingredients with non-toxic, inert, solid or liquid carriers which are suitable for topical treatment and which are customary in such preparations.

Convenient for topical use are about 0.005-2%, preferably 0.01-1%, solutions, lotions, salves or creams.

An antioxidant, e.g., tocopherol, N-methyl-γ-tocopheramine as well as butylated hydroxyanisole or butylated hydroxytoluene, can be admixed with the preparations if desired. Furthermore, the preparations can contain other active substances, especially radiation-protection agents such as silicates, talc, titanium dioxide, zinc oxide or cinamic acid derivatives such as <Parsol>.

The following Examples illustrate the invention further. The temperatures are given in degrees Celsius.

EXAMPLE 1

45 g of 3,7-dimethyl-9-(2,6,6-trimethyl-1-cyclohexen-1-yl)-2-(Z),4,6,8(E)-nonatetraenoic acid are suspended in 750 ml of dry acetonitrile and treated with 22.8 g of 1,8-diazabicyclo-(5,4,0)undec-7-ene. After stirring at room temperature under argon and with the exclusion of light for 1 hour, 30.8 g of iodomethyl acetate in 30 ml of acetonitrile are added thereto. The reaction mixture is stirred at 80° for 3 hours and at room temperature overnight. Then, the solvent is removed on a rotary evaporator in a vacuum and the residue is dissolved in 500 ml of methylene chloride. The organic phase is extracted once with 250 ml of a dilute hydrochloric acid solution and twice with in each case 250 ml of a saturated sodium chloride solution. The methylene chloride phase is separated, dried over sodium sulphate and filtered over a column containing 150 g. of neutral aluminium-oxide. The adsorption agent is rinsed with 300 ml of methylene chloride and the eluate is concentrated on a rotary evaporator in a vacuum. Crystallization of the oily residue from ethanol given yellow crystals. The mother liquor of the crystallization if concentrated in a vacuum and the residual oil is purified by chromatography over 300 g of silica gel with methylene chloride-petroleum ether-tert.butyl methyl ether 62:130:8. There thereby separates a further fraction of the desired product which is combined with the solid from the first crystallization. After renewed crystallization from ethanol there are obtained 18.3 g of methylene acetate 3,7-dimethyl-9-(2,6,6-trimethyl-1-cyclohexen-1-yl)-2-(Z),4,6,8(E)-nonatetraenoate with a melting point of 56°–58°. Rf (silica gel/methylene chloride-petroleum ether-tert.butyl methyl ether 62:130:8) 0.44.

EXAMPLE 2

Ethylene acetate 3,7-dimethyl-9-(2,6,6-trimethyl-1-cyclohexen-1-yl)-2-(Z),4,6,8(E)-nonatetraenoate is manufactured analogously to Example 1 from 45 g of 3,7-dimethyl-9-(2,6,6-trimethyl-1-cyclohexen-1-yl)-2-(Z),4,68(E)-nonatetraenoic acid, 22.8 g of 1,8-diazabicyclo(5,4,0)undec-7-ene, 20.4 g of 1-chloroethyl acetate and 10 g of NaI. Crystallization from ethanol gives a first fraction of the desired product. After evaporation of the mother liquor, the residue is chromatographed over 350 g of silica gel with methylene chloride/petroleum ether/tert-butyl methyl ether (25:71:4) as the elution agent, whereby a further fraction of the product is obtained. Crystallization of the two fractions leads to 23.5 g of yellow crystals with a melting point of 84°–86°. Rf (silica gel/methylene chloride-petroleum ether-tert.butyl methyl ether 62:130:8) 0.42.

EXAMPLE 3

A hydrogel can have the following composition:

| | | |
|---|---|---|
| Active substance | | 0.2 g |
| Hydroxypropylcellulose | | 2.0 g |
| Ethanol | | 50.0 g |
| Propylene glycol | | 20.0 g |
| Butylated hydroxytoluene | | 0.05 g |
| D,L-α-Tocopherol | | 0.15 g |
| Water | ad | 100.0 g |

Production

The active substance, the antioxidant and the preserving agent are dissolved in ethanol. After admixture of the propylene glycol-water solution the mixture is left until the gel former has swollen clear.

EXAMPLE 4

A lipogel can have the following composition:

| | | |
|---|---|---|
| Active substance | | 0.1 g |
| D,L-α-Tocopherol | | 0.15 g |
| Aerosil 200 | | 8.0 g |
| Triglyceride, medium-chain | ad | 100.0 g |

Production

The active substance and the antioxidant are dissolved in the triglyceride. The gel-former is then incorporated while stirring.

EXAMPLE 5

A solution can have the following composition:

| | | |
|---|---|---|
| Active substance | | 0.05 g |
| Butylated hydroxytoluene | | 0.05 g |
| Ethanol | | 50.0 g |
| Polyethylene glycol 400 | ad | 100.0 g |

Production

The active substance and the preserving agent are dissolved in ethanol. The polyethylene glycol is added to this solution.

EXAMPLE 6

An oil-in-water cream can have the following composition:

| | | |
|---|---|---|
| Active substance | | 0.2 g |
| Butylated hydroxytoluene | | 0.05 g |
| Polyoxyethylene-sorbitan monostearate | | 6.5 g |
| Cetyl alcohol | | 10.0 g |
| Vaseline, white | | 25.0 g |
| Glycerine | | 10.0 g |
| Benzoic acid | | 0.2 g |
| Water | ad | 100.0 g |

Production

The active substance is incorporated into the molten fatty phase at 70°–75°. Glycerine, the emulsifier and benzoic acid are added to the water. The two phases are homogenized at 70° and left to cool to room temperature while homogenizing.

EXAMPLE 7

| | |
|---|---|
| Active substance | 0.2 g |
| Hydroxylated butyltoluene | 0.05 g |
| D,L-α-Tocopherol | 0.15 g |
| Paraffin, viscous | 40.0 g |
| Vaseline, white | 45.0 g |

-continued

| | | |
|---|---|---|
| Castor oil, hardened | ad | 100.0 g |

Production

The active substance is incorporated into the 80° hot fatty phase and the mixture is left to cool to room temperature while stirring.

I claim:

1. Ethylidene acetate 3,7-dimethyl-9-(2,6,6-trimethyl-1-cyclohexen-1-yl)-2(Z),5,7,8(E)-nonatetraenoate.

2. A method for the topical treatment of dermatological disorders and for the treatment of aging skin comprising the application of the compound of claim 1 in an amount sufficient to treat said disorders or aging skin.

* * * * *